United States Patent [19]

Christy et al.

[11] 4,425,269

[45] Jan. 10, 1984

[54] METABOLICALLY PROTECTED ANALOGS OF NEUROTENSIN

[75] Inventors: Marcia E. Christy, Perkasie; Kenneth L. Shepard, West Point; Robert G. Strachan, Warrington; Sandor L. Varga, Harleysville, all of Pa.

[73] Assignee: Merck & Co., Inc., Rahway, N.J.

[21] Appl. No.: 385,746

[22] Filed: Jun. 7, 1982

[51] Int. Cl.$^3$ .......................................... C07C 103/52
[52] U.S. Cl. ............................................. 260/112.5 R
[58] Field of Search ................................ 260/112.5 R

[56] References Cited

PUBLICATIONS

J. Med. Chem., 24, 370–376 (198), St. Pierre et al.
J. Biol. Chem., 251, 7035–7044 (1976), R. Carraway et al.
Mol. Pharm., 18, 11–19 (1980), P. Kitabgi et al.
J. Med. Chem., 20, No. 11, 1409–1412 (1977), J. E. Rivier et al.
Chem. Abstr., vol. 97 (1982), 17376c.
Chem. Abstr., vol. 96 (1982), 116462p.
Chem. Abstr., vol. 95 (1981), 91356w.

*Primary Examiner*—Delbert R. Phillips
*Attorney, Agent, or Firm*—Salvatore C. Mitri; Rudolph J. Anderson

[57] ABSTRACT

There are disclosed metabolically protected linear analogs of the carboxy terminal pentapeptide fragment of the tridecapeptide, neurotensin.

6 Claims, No Drawings

METABOLICALLY PROTECTED ANALOGS OF NEUROTENSIN

BACKGROUND OF THE INVENTION

The tridecapeptide, neurotensin (NT) is known to have a wide variety of pharmacological effects, including those common to peptides in the kinen group. NT is also known to have activity within the central nervous system producing hypothermia, a reduction in locomotor activity and an antinocisponsive effect in rodents. These pharmacological actions of NT suggest that the peptide is a neurotransmitter or neuromodulator. Consequently, this tridecapeptide holds a great deal of potential for a host of therapeutic applications.

A solid-phase method for preparing peptides, including NT, and analogs of NT modified at the C-terminal end of the molecule is described by St. Pierre, et al. [*J. Med. Chem.*, 24, 370–376 (1981)].

The structural requirements for biological activity of NT and methods for obtaining partial sequences of this tridecapeptide have been reported by R. Carraway, et al., [*J. Biol. Chem.*, 251, 7035–7044 (1976)].

The binding affinity of NT and NT analogs has been examined by P. Kitabgi, et al., [*Mol. Pharm.* 18, 11–19 (1980)] and the activity relationships of a series of NT analogs and their relative potencies has been explored by J. E. Rivier, et al. [*J. Med. Chem.*, 20, No. 11, 1409–1412 (1977)]. Among their findings, J. E. Rivier, et al., observed that substitutions in positions 1–9 of the tridecapeptide yielded active peptides, but that modifications in positions 10–13 significantly decreased biological activity.

These references indicate that the smallest NT peptide fragment that exhibits NT activity is the C-terminal hexapeptide. Although the corresponding pentapeptide fragment exhibits NT-like activity, it is less potent then both NT itself and its hexapeptide fragment.

SUMMARY OF THE INVENTION

It has been surprisingly found that blocked pentapeptide derivatives of NT exhibit substantially the same activity and have substantially the same potency as the tridecapeptide. These blocked pentapeptide derivatives are linear analogs of the carboxy-terminal fragment of NT and can be represented by the general formula:

α-A-B-Pro-Tyr-C-D-Y    (I)

wherein:

A is another blocked amino acid (such as alkoxycarbonyl-4-aminobutyric acid, alkoxycarbonyl-β-alanine, and the like); alkoxycarbonyl;

B is a basic amino acid residue (such as 2,4-diamino butyric acid, lysine, arginine, ornithine, homoarginine, and the like);

C is isoleucine, norleucine, or valine;

D is leucine or norleucine; and,

Y is a terminal group (such as carboxylic acid), ester (loweralkyl or aralkyl), amide (unsubstituted amino, aralkyl, or dimethylaminoethyl), and the like.

Preferred pentapeptide derivatives of Formula I are those wherein:
A is t-butyloxycarbonyl;
B is lysine or 2,4-diaminobutyric acid;
C is isoleucine;
D is leucine; and,
Y is OH, OCH$_3$ or OCH$_2$C$_6$H$_5$.

More preferred pentapeptide derivatives of Formula I are those wherein:
A is t-butyloxycarbonyl;
B is lysine;
C is isoleucine;
D is leucine; and,
Y is OH or OCH$_3$.

More preferred pentapeptides of Formula I are those wherein:
A is t-butyloxycarbonyl;
B is lysine;
C is isoleucine;
D is leucine; and,
Y is OH.

Processes by which the blocked pentapeptide derivatives of the invention can be obtained are illustrated in the following Reaction Schemes wherein Y is as defined above, 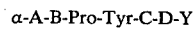 denotes a resin such as a chloromethylated polystyrene-divinylbenzene copolymer, "ClZ" is chlorobenzyloxycarbonyl, "Inoc" is isonicotinyloxycarbonyl, and the remaining abbreviations used are those commonly employed in the practice of peptide chemistry and are well known to those skilled in the art.

REACTION SCHEME I

Boc—Leu—O ®    (II)

↓ SPPS

Boc—Lys(2-ClZ)—Pro—Tyr—Ile—Leu—O ®    (III)

↓ CH$_3$OH/Et$_3$N

Boc—Lys(2-ClZ)—Pro—Tyr—Ile—Leu—OCH$_3$    (IV)

↓ H$_2$; Pd/C

Boc—Lys—Pro—Tyr—Ile—Leu—OCH$_3$    (Ia)

REACTION SCHEME II

Boc—Leu—O ®

↓ SPPS

Boc—Lys(Inoc)—Pro—Tyr—Ile—Leu—O ®    (V)

↓ CH$_3$OH/Et$_3$N

Boc—Lys(Inoc)—Pro—Tyr—Ile—Leu—OCH$_3$    (VI)

↓ YNH$_2$ (VII)

Boc—Lys(Inoc)—Pro—Tyr—Ile—Leu—NHY    (VIII)

↓ H$_2$; Pd/C

Boc—Lys—Pro—Tyr—Ile—Leu—NHY    (Ib)

As illustrated in Reaction Scheme I, appropriately blocked peptide or amino acid (II) such as leucine (Leu)

blocked with tert-butyloxycarbonyl (Boc) and bound to a resin (O®) is subjected to a standard solid phase peptide synthesis (SPPS), such as those described in the above-identified references which are incorporated herein by reference, to obtain blocked pentapeptide (III). Blocked pentapeptide (III) is then suspended in a suitable organic solvent such as methanol and triethylamine and stirred at room temperature to afford blocked pentapeptide methyl ester (IV). By means of catalytic hydrogenation such as over Pd/C, blocking group 2-ClZ is removed to obtain a blocked pentapeptide compound (Ia) of the invention.

The process illustrated in Reaction Scheme II is similar to that of Reaction Scheme I except that blocking group Inoc is used in place of 2-ClZ in blocked pentapeptides (V) and (VI) and the terminal ester group (VI) is replaced by an amine (VII) to produce amide-terminated-blocked pentapeptide (VIII). Upon catalytic hydrogenation of blocked pentapeptide (VIII), a further blocked pentapeptide (Ib) of the invention is obtained.

The following Examples are set forth to further illustrate the protected pentapeptides of the invention and are intended to be exemplary and not limitative of the invention.

EXAMPLE 1

Synthesis of BOC-Lys-Pro-Tyr-Ileu-Leu OCH$_3$ 3.5 g of BOC-Lys(Z)-Pro-Tyr-Ile-Leu-O-®, containing approximately 2 mmoles of peptide, was treated with 150 ml 10% Et$_3$N-CN$_3$OH for 24 hrs. The solution was separated from the resin by filtration and the resin was treated with 150 ml 10% Et$_3$N-CN$_3$OH for another 24 hrs. The resin was separated from the solution by filtration. The CH$_3$OH solutions were combined and the solvent removed in vacuo.

The residue was dissolved in a mixture of 100 ml CH$_3$OH, 25 ml H$_2$O and 25 ml HOAc. 500 mg 20% Pd(OH)$_2$/C was added and the solution was hydrogenolyzed overnight at 40 psi of H$_2$. The catalyst was removed by filtration and the product purified by chromatography on Sephadex G-25 in 50% HOAc. The freeze-dried product was characterized by TLC, HPLC, amino acid analysis after acid hydrolysis and p.m.r.

EXAMPLES 2-5

Using the appropriate starting materials, the following products were also prepared by the procedures described in Example 1:
Ex. 2 Box-β-Ala-Lys-Pro-Ile-Leu-OCH$_3$
Ex. 3 Boc-Gaba-Lys-Pro-Tyr-Ile-Leu-OCH$_3$
Ex. 4 Boc-Lys-Pro-Tyr-Leu-OCH$_3$
Ex. 5 Boc-Lys-Pro-Tyr-Val-Leu-OCH$_3$

EXAMPLE 6

BOC-A2bu-Pro-Tyr-Ile-Leu-OCH3

(TFA) Pro-Tyr-Ile-Leu-O ® was prepared by conventional solid phase peptide synthesis and transesterified by essentially the same procedure described in Example 1. The tetrapeptide methyl ester, 750 mg (1.45 mmole), and 617 mg (1.45 mmole) of α-Boc-A2bu (Z) were dissolved in 10 ml of freshly degassed dimethylformamide (DMF). The solution was cooled to 5° C. and treated with 440 mg (1.6 mmole) of diphenylphosphoryl azide in 1 ml DMF, followed by 609 mg of solid NaHCO$_3$. After stirring at 5° C. for 48 hours, the mixture was filtered and the filtrate was evaporated to dryness in vacuo. The residue was chromatographed on silica gel, eluting with CHCl$_3$—CH$_3$OH-H$_2$O (95:5:0.5). Appropriate fractions, as determined by TLC, were pooled and evaporated to dryness in vacuo leaving the blocked pentapeptide methyl ester as the residual oil.

This oil was dissolved in 10 ml of HCOOH (88%)—CH$_3$OH (5:95 v/v) and added to a stirred mixture of 200 mg of 10% Pd/C and 10 ml of HCOOH (88%)—CH$_3$OH (5:95 v/v) at room temperature and under nitrogen. After 1 hour, catalyst was separated by filtration and washed with CH$_3$OH (3×3 ml) and H$_2$O (2×5 ml). The combined filtrate and washings were evaporated in vacuo. The residue was purified by chromatography on Sephadex G-25 in 50% HOAc. After freeze-drying, the product was characterized by TLC, HPLC, p.m.r., and amino acid analysis after acid hydrolysis.

EXAMPLE 7

Boc-Lys-Pro-Tyr-Ile-Leu

Boc-Lys-Pro-Tyr-Ile-Leu-OCH$_3$, approximately 1.5 mmole obtained as described in Example 1, dissolved in a mixture of 100 ml H$_2$O and 50 ml tetrahydrofuran (THF), was hydrolyzed at pH 12.5 for 4.5 hours. The pH of the solution was then adjusted to 7.0 with 3 N HCl and the solvents were removed in vacuo. The residue was dissolved in 200 ml H$_2$O and after the pH was adjusted to 6.8, the aqueous solution was extracted with 200 ml, then with 100 ml n-BuOH. The butanol extracts were combined and the solvent removed in vacuo, yield 1.0 g of the product. It was characterized by TLC, HPLC, amino acid analysis after acid hydrolysis and pmr.

EXAMPLE 8

Boc-Lys-Pro-Tyr-Ile-Nle-OCH$_3$

Boc-Lys (2-ClZ)-Pro-Tyr-Ile-O ® was prepared by conventional solid phase peptide synthesis, transesterified by essentially the same procedures described in Example 1, and saponified by essentially the same procedures described in Example 7. The product thus obtained was purified by chromatography on silica gel, eluting with EtOAC-pyridine-HOAC-H$_2$O (90:5:1:1). Appropriate fractions, as determined by TLC, were pooled and evaporated to dryness in vacuo, leaving the blocked tetrapeptide as the residual oil.

This oil, 552 mg (0.7 mmole) and 127 mg (0.7 mmole) of norleucine methyl ester hydrochloride were dissolved in 5 ml of freshly degassed DMF. The solution was cooled to 5° C. and treated with 385 mg (1.4 mmole) of diphenylphosphoryl azide in 0.5 ml DMF, followed by 210 mg (2.5 mmole) of solid NaHCO$_3$. After stirring at 5° C. for 6 days, the mixture was filtered and the filtrate was evaporated to dryness in vacuo, leaving the blocked pentapeptide methyl ester as the residual oil.

This oil was deprotected by catalytic hydrogenolysis by essentially the same procedures described in Example 1. The product thus obtained was purified by chromatography on silica gel, eluting with EtOAC-pyridine-HOAC-H$_2$O (15:5:1:2). Appropriate fractions, as determined by TLC, were pooled and evaporated to dryness. The residue was desalted by gel filtration through Sephadex G-25 in 50% HOAC. The freeze dried product was characterized by TLC, HPLC, pmr, and amino acid analysis.

EXAMPLE 9

α-Boc-Lys-Pro-Tyr-Ile-Leu-NHCH$_2$C$_6$H$_5$

Step A: Boc-Lys(Inoc)-Pro-Tyr-Ile-Leu-OCH$_3$

A mixture of Boc-Lys(Inoc)-Pro-Tyr-Ile-Leu-O ® (8.80 g, 5 mmole) and 10% EtzN in methanol (400 ml) was stirred in a closed vessel for 18 hrs. and filtered. The solid on the filter was washed with methanol (5×40 ml) and the combined filtrates stripped to dryness. The residue was redissolved in methanol, stripped in vacuo and dried to constant weight, 3.55 g.

Step B: Boc-Lys(Inoc)-Pro-Tyr-Ile-NHNH$_2$

A solution of the ester from Step A (1.76 g, 2 mmols), hydrazine (1 ml) and methanol (9 ml) was stirred for 3 hrs at 25°, then kept at −20° for 3 days. The solvent was removed in vacuo and the residue was redissolved and restripped from methanol (3×10 ml). The residue was triturated with H$_2$O, filtered and the solid washed with H$_2$O until the washings gave a negative Tollen's test. Drying to constant weight in vacuo gave 1.32 g.

Step C: Boc-Lys(Inoc)-Pro-Tyr-Ile-Leu-NHCH$_2$C$_6$H$_5$

To a solution of the hydrazide from Step B (1.2 g, 1.36 mmols) in freshly degassed DMF (6 ml) at −20° there was added 1.25 ml (6.8 mequiv) of 5.42 N HCl in THF followed by isoamylnitrite (0.19 ml) in portions until a faint positive starch-iodine test was obtained after 10 min (total time = 1 hr). An aliquot (2.5 ml) was removed, benzyl amine (0.055 ml, 0.5 mmol) was added, the pH was adjusted to 7.6 with diisopropylethylamine and the solution stored at −20°. After 7 days, the solvent was removed in vacuo, the residue triturated with H$_2$O and the resulting solid filtered and dried, 0.445 g.

Step D: Boc-Lys-Pro-Tyr-Ile-Leu-NHCH$_2$C$_6$H$_5$

Nitrogen was bubbled through a solution of the amide (0.430 g, 0.45 mmol) in ethanol (8 ml) and 5% acetic acid (5 ml). Palladium on charcoal (100 mg, 10%) was added and hydrogen was bubbled through the stirred reaction mixture for 2 hrs. The mixture was filtered through Supercel and the filter cake washed with ethanol—5% acetic (1:1, 10 ml) followed by ethanol (15 ml). The combined filtrate and washings were concentrated in vacuo, the residue was dissolved in 2 N acetic acid, applied to a Sephadex G-25SF column and eluted with 2 N acetic acid. The fractions containing the desired material were combined, concentrated in vacuo and the mixture freeze-dried to give 0.314 g of white powder (HPLC 95% purity, Spinco analysis satisfactory).

EXAMPLE 10

Boc-Lys-Pro-Tyr-Ile-Leu-NHCH$_2$CH$_2$N(CH$_3$)$_2$

Following essentially the same procedures described in Example 9, the pentapeptide azide obtained in Step C (Example 9) was reacted with dimethylaminoethylamine and the resulting amide was deprotected by catalytic hydrogenolysis as in Step D (Example 9) to provide the product. It was characterized by TLC, HPLC, and amine acid analysis after acid hydrolysis.

EXAMPLE 11

α-Boc-Lys-Pro-Tyr-Ile-LeuOCH$_2$C$_6$H$_5$

Step A: α-Boc-Lys(Inoc)-Pro-Tyr-Ile-LeuOH

A solution of α-Boc-Lys(Inoc)-Pro-Tyr-Ile-LeuOCH$_3$ (0.882 g), from Example 9, Step A, dioxane (20 ml) and methanol (10 ml) was adjusted to pH 12 with 1 N NaOH. After 1 hr (25°), the pH of the solution was adjusted to pH 6 and concentrated to dryness in vacuo, 0.914 g.

Step B: α-Boc-Lys(Inoc)-Pro-Tyr-Ile-LeuOCH$_2$C$_6$H$_5$

The acid (0.42 g) from Step A was converted to its cesium salt by dissolving in ethanol (15 ml) and water (2 ml), adjusting the pH of the solution to 7.2 by the addition of 20% CsCO$_3$ solution. This solution was concentrated in vacuo (35°), treated with DMF and restripped (2×40 ml). The resulting dried solid was dissolved in a minimum quantity of freshly degassed DMF and benzyl chloride (0.067 g) was added. After 24 hrs, the solution was concentrated in vacuo, treated with ether, petroleum ether, then water to give 0.53 g off-white solid.

Step C: α-Boc-Lys-Pro-Tyr-Ile-LeuOCH$_2$C$_6$H$_5$

The ester from Step B was dissolved in ethanol (8 ml), 5% acetic acid (5 ml) was added, nitrogen bubbled through the solution and 10% Pd/C (0.135 g) was added. Hydrogen was bubbled through the solution for one hr., the reaction mixture was filtered through Supercel, washed with ethanol and 5% acetic acid and the combined filtrates were concentrated in vacuo. The resulting oil was chromatographed over silica gel (50 g) eluting with CHCl$_3$-MeOH-H$_2$O (80-20-0.5) to give 0.099 g of white solid (HPLC 85%, Spinco satisfactory).

I claim:

1. A blocked pentapeptide derivative compound of neurotensin having the formula:

α-A-B-Pro-Tyr-C-D-Y    (I)

wherein:
A is another blocked amino acid selected from the group alkoxycarbonyl-4-aminobutyric acid; alkoxycarbonyl-β-alanine; and, alkoxycarbonyl;
B is a basic amino acid residue selected from the group 2,4-diaminobutyric acid, lysine, arginine, ornithine, and homoarginine;
C is a member of the group: isoleucine, norleucine, or valine;
D is a member of the group: leucine or norleucine; and,
Y is OH,OCH$_3$,OCH$_2$,C$_6$H$_5$, NH$_2$,NH(lower alkyl),NH(aralkyl) or NH(dimethylaminoethyl).

2. A compound of claim 1 wherein said ester is a member of the group: loweralkyl and aralkyl.

3. A compound of claim 1 wherein said amide is an unsubstituted amide, aminoaralkyl, and dimethylaminoethyl.

4. A blocked pentapeptide derivative compound of neurotensin having the formula:

α-A-B-Pro-Tyr-C-D-Y    (I)

wherein:
A is t-butyloxycarbonyl;
B is lysine or 2,4-diaminobutyric acid;
C is isoleucine;

D is leucine; and,
Y is OH, OCH$_3$ or OCH$_2$C$_6$H$_5$.

5. A blocked pentapeptide derivative compound of neurotensin having the formula:

α-A-B-Pro-Tyr-C-D-Y (I)

wherein:
A is t-butyloxycarbonyl;
B is lysine;
C is isoleucine;
D is leucine; and,
Y is OH or OCH$_3$.

6. A blocked pentapeptide derivative compound of neurotensin having the formula:

α-A-B-Pro-Tyr-C-D-Y (I)

wherein:
A is t-butyloxycarbonyl;
B is lysine;
C is isoleucine;
D is leucine; and,
Y is OH.

* * * * *